United States Patent [19]
Shanbrom

[11] Patent Number: 6,045,787
[45] Date of Patent: Apr. 4, 2000

[54] PROTECTION OF LABILE PROTEINS DURING IODINE DISINFECTION

[75] Inventor: Edward Shanbrom, Santa Ana, Calif.

[73] Assignee: Shanbrom Technologies LLC, Ojai, Calif.

[21] Appl. No.: 09/146,383

[22] Filed: Sep. 1, 1998

[51] Int. Cl.$^7$ .............................. A61K 31/79; A61K 9/36; A61K 9/14; A61K 33/36
[52] U.S. Cl. ...................... 424/78.24; 424/480; 424/488; 424/667; 424/668
[58] Field of Search .................................. 424/78.24, 480, 424/488, 667, 668

[56] References Cited

U.S. PATENT DOCUMENTS

| | | | |
|---|---|---|---|
| 5,019,495 | 5/1991 | Shanbrom | 435/1 |
| 5,128,149 | 7/1992 | Shanbrom | 424/529 |
| 5,128,150 | 7/1992 | Shanbrom | 424/533 |
| 5,186,945 | 2/1993 | Shanbrom | 424/529 |
| 5,360,605 | 11/1994 | Shanbrom | 424/78.08 |
| 5,370,869 | 12/1994 | Shanbrom | 424/78.22 |
| 5,589,072 | 12/1996 | Shanbrom | 210/638 |
| 5,609,864 | 3/1997 | Shanbrom | 424/78.08 |
| 5,639,376 | 6/1997 | Shanbrom | 210/645 |

FOREIGN PATENT DOCUMENTS 9748482  12/1997  WIPO .

*Primary Examiner*—Kevin E. Weddington
*Attorney, Agent, or Firm*—Stefan J. Kirchanski, Esq.; Graham & James LLP

[57] ABSTRACT

Mixtures of iodine source resin with iodine capture resin have been found to provide effective disinfecting of protein containing solutions such as plasma. These mixtures can be used in a chromatographic manner to effectively disinfect solutions while causing minimal damage to labile proteins such as clotting factors. Mixed resins containing equivalent amount of iodine source and iodine capture (50:50) are effective in many cases. If protein damage is still occurring, the ideal mixture may be one containing a lower amount of iodine (e.g. 25:75 or even 5:95). If disinfecting properties prove inadequate, ratios can be increased (e.g. 80:20). Surprisingly, the mixed resins also spare tissue components such as red blood cells and platelets. In some cases mixed resins are even useful in a batch procedure where the resin is removed by centrifugation or filtration at the end of a treatment period.

10 Claims, No Drawings

PROTECTION OF LABILE PROTEINS DURING IODINE DISINFECTION

BACKGROUND OF THE INVENTION

1. Field of the Invention

The present application concerns the use of iodine containing materials to disinfect protein-containing solutions such as blood, blood fractions, enzymes and vaccines

2. Description of Related Art

There is an almost daily discovery of some exotic new pathogen that is transmitted by blood transfusion or by intimate contact. Human immunodeficiency virus (HIV, the causative agent of AIDS) and the plethora of new hepatitis viruses leap to mind, but many other serious disease-causing agents that are communicated in similar ways are being discovered constantly. It seems that the human habit of cooking its prey has long shielded us from many viruses that require blood to blood transmission. Now modern medicine with its use of transfusions and blood and tissue fractions has removed that shield. Many workers have been experimenting with a variety of disinfecting chemical and physical agents to try to eliminate virus and other disease-causing agents from blood and other medical materials.

The present inventor has disclosed a considerable number of inventions based around the use of free elemental iodine to kill or inactivate a large range of microbes (bacteria, virus and other pathogens) particularly in protein-containing solutions such as human blood, human plasma or fractions thereof. The reader's attention is drawn to U.S. Pat. Nos. 5,019,495; 5,128,149; 5,128,150; 5,186,945; 5,360,605; 5,370,869; 5,589,072; and 5,609,864 by the present inventor. The contents of these patents are incorporated herein by reference.

Initially some workers objected to these iodine methods because they feared excessive amounts of free (elemental) iodine or combined iodine would be left in the disinfected product. However, the present inventor was able to demonstrate that chromatographic "capture" techniques could overcome these objections. By capture is meant the use of a resin or other material that binds iodine so strongly as to effectively remove all free iodine from a solution flowing through the capture material. Of course, a capture material that binds free or elemental iodine cannot remove covalently bound iodine. However, experimentation has shown that the organic reactions by which iodine becomes covalently bound are relatively slow. If a protein solution is rapidly iodinated by contact with an iodine source and then immediately passed through an effective capture agent, the amount of covalently bound iodine is negligible.

Thus, the major problem with the iodine system is not the presence of iodine in the final product. Rather, the interaction of the proteins with iodine may result in permanent alteration of the protein even though little or no iodine remains bound. This denaturation is, perhaps, most obvious as loss of enzymatic activities. The complex system by which human plasma forms a clot is especially liable to such damage. Also subtle damage can be apparent in the loss of growth factors as when an iodine-treated material is less effective at supporting cell growth in tissue culture.

SUMMARY OF THE INVENTION

Mixtures of iodine source resin with iodine capture resin have been found to provide effective disinfecting of protein-containing solutions such as plasma. These mixtures can be used in chromatographic columns to effectively disinfect protein-containing solutions while causing minimal damage to labile proteins such as blood clotting factors. Mixed resins containing equivalent amount of iodine source and iodine capture (50:50 mixtures) are effective in many cases in obtaining complete disinfecting with little protein damage. If protein damage is still occurring, the ideal mixture may be one containing a lower amount of iodine (e.g. 25:75 or even 5:95). If disinfecting properties prove inadequate, ratios can be increased (e.g. 80:20). Surprisingly, the mixed resins also spare tissue components such as red blood cells and platelets. In some cases mixed resins are even useful in a batch procedure where the resin is removed by centrifugation or filtration at the end of a treatment period. By mixing iodinated resin with non-iodinated resin effective disinfecting can be achieved with levels of iodine that are ineffective when used without the added non-iodinated component. The inventor has termed this paradoxical effect the "spider web." It is theorized that the limiting factor in iodine disinfecting is not the total percentage of iodine but rather the surface area over which the iodine is spread. By admixing non-iodinated capture resin with iodinated resin the effective area is greatly increased because the non-iodinated capture resin rapidly picks up a surface coating of iodine which is effective at disinfecting. At the same time the non-iodinated material serves as an iodine "sink" and prevents over-iodination of the material being disinfected. Tests have shown that the "spider web" effect also protects labile flavors as in fruit juices, milk and other liquid foods. This presents a non-heat method for disinfecting liquid food products without damaging flavor, etc.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a mixed resin (iodine source:iodine capture) system for disinfecting protein-containing solutions without causing damage to labile enzymes or other constituents.

As explained above, the present inventor has discovered that treatment of protein-containing solutions with iodine followed by removal of the free iodine is a remarkable disinfectant killing both viral and bacterial contaminants in the protein solution. A concern with this technique is the possibility of iodine damage to delicate proteins. While many proteins appear resistant to disinfecting concentrations of iodine, others are definitely labile. This also applies to liquid foods where the iodine damage is apparent as a change in flavor. Excess iodination can be dealt with by lowering the concentration of available iodine and by increasing the flow rate of the solution to be disinfected so that iodine contact time is diminished. Unfortunately, either of these approaches readily results in insufficient iodine treatment and a failure to achieve adequate disinfecting. Even where the amount of available iodine is rather severely limited some materials will still take up an excess of iodine.

This problem is especially obvious when one attempts to disinfect liquids containing cells or cellular components. For example, when solutions containing red blood cells (RBCs) are processed with iodine, the RBCs rapidly absorb a large quantity of iodine. This is indicated by a darkening of the color of the RBCs followed shortly by a noticeable increase in hemolysis. If 20 ml of fresh whole blood is mixed with 1 g of iodinated Q Sepharose (10% by weight elemental iodine) (Q-Sepharose is a carbohydrate-based gel filtration medium made by Amersham-Pharmacia Biotech) and the resin allowed to settle, excess iodine will be transferred into the blood cells. The initial indication of excess iodine is a pronounced darkening of the cells. Within 24 hrs the treated blood becomes profoundly hemolyzed. On the other hand, if 20 ml of fresh whole blood is mixed with 1 g of Purodine resin (10% by weight elemental iodine) (an iodinated styrene-divinylbenzene ion exchange resin manufactured by the Purolite Corporation) there is little, if any excess hemolysis (as compared to control blood) after 24 hrs. The difference appears to be that iodine is more tightly bound to the Purolite resin than to the Q-Sepharose. Presumably, the Purolite resin binds iodine more avidly than does the RBCs. This prevents the RBCs from taking up excess iodine. Of course, if the iodine source binds iodine with excessive affinity, it will prevent the sample from being excessively iodinated, but it may also prevent contaminating microbes from being iodinated. That is, it may be ineffective at disinfecting. "Affinity" is the term used herein to express the strength by which one substance is bound to another. It is generally used here to describe the binding of elemental iodine to an insoluble iodine source material.

To further demonstrate the effect of differences in iodine affinity the bactericidal properties of a high affinity (Purolite) and lower affinity (Sepharose) resin were tested on whole blood. Whole blood was spiked with a heavy suspension of *Escherichia. coli*. Samples (0.1 g) of either Purodine or iodinated Sepharose were added to 20 ml aliquots of spiked blood in centrifuge tubes. The tubes were mixed thoroughly and allowed to incubate for 30 min at room temperature. The resin was removed by filtration through CF-150 (polyvinyl acetal sponge manufactured by Merocel Corporation of Mystic, Conn.) and 1 ml aliquots of the blood samples were spread onto nutrient agar and incubated at 37° C. for 24 hr. After this incubation the plates were observed for bacterial growth. Hemolysis was judged at the time that filtered samples were placed on the plates. Results are given in Table 1.

TABLE 1

|  | Bacterial Growth | Hemolysis |
| --- | --- | --- |
| Positive Control | +++ | No hemolysis |
| Negative Control (no bacterial) | No Growth | No hemolysis |
| Q-Sepharose | + | Moderate Hemolysis |
| Purolite | ++ | No hemolysis |

These results indicate that the resin that showed high affinity for iodine caused no hemolysis but was less effective at killing bacteria than the lower affinity resin. Presumably the kill caused by the iodinated Q-Sepharose could be improved by increasing the amount of resin or the incubation time but at the expense of even more hemolysis. Purodine resin kill could also be similarly improved but the amount of resin and/or the required incubation time might be truly excessive. Increasing the amount of resin to 0.2 g in each case resulted in total bacterial kill with iodinated Q-Sepharose and improved kill with Purodine albeit with increased hemolysis as well. It could also be demonstrated that this concentration of Q-Sepharose was effective against added *Staphylococcus epidermis* and *Pseudomonas aeruginosa* as well. It should be noted that polyvinyl acetal and cross-linked polyvinyl pyrollidone, and iodinated polyvinyl acetal and iodinated cross-linked polyvinyl pyrollidone can also be used for iodine capture and iodine source, respectively.

In theory, at least, it should be possible to match any particular substance to be disinfected with an iodine source of just the correct affinity to ensure disinfecting without excess iodination. There are, of course, several variables besides just affinity. The percentage of iodine on the source material is of importance because as more and more iodine is bound to the source, the source becomes saturated and holds the additional iodine with less affinity. Thus, for sources with relatively high iodine percentages removal of iodine from the source is controlled more by the solubility of iodine in the medium than by binding of iodine to the source. Iodine is only very poorly soluble in most aqueous media. Thus, what really controls the effective level of iodine (assuming that the source is saturated) is the residence time of the material to be disinfected (i.e., the flow rate of the material through the iodine source) and the presence of iodine binding substances in the material to be disinfected. That is, many proteins readily bind considerable iodine; if a protein solution flows relatively slowly over a saturated iodine source, the protein molecules will become saturated. If the protein is at all labile in the presence of iodine, the protein will be damaged unless an iodine capturing agent is able to remove the iodine before damage occurs. The other very important factor is the available surface area of the iodine donating material. Because the iodine is only slightly soluble, much of the inactivation of pathogens probably occurs through contact with the iodine source in which a lethal quantity of iodine is transferred to the pathogen. Thus, a large volume of relatively low iodine level resin may be much more effective than a smaller volume of resin with a high iodine level.

The variables, then, are relatively few. For optimal disinfection of a dissolved protein (or for a suspended cellular component) an iodine source must bind iodine with a lower affity than the material to be disinfected. However, the source must bind with sufficient affinity to prevent damage by excess iodination. Further there must be a sufficient surface area of iodine to effectively contact all to the material to be disinfected. Damage from over-iodination can be reduced or prevented by decreasing the contact time between the source and material to be disinfected (faster flow rates). Damage can also be reduced or prevented by providing an iodine binding (capture) material with sufficient affinity to strip the free iodine rapidly from the treated material. The problem remains that the precise balance of these factors is difficult to achieve. If the affinity of the iodine source material could be readily adjusted, it should be possible to disinfect using a relatively rapid flow rate. However, in the usual chromatographic column used for this purpose a sufficiently low affinity iodine source to ensure adequate disinfecting often results in protein damage because sensitive proteins are damaged within the time taken for the sample to flow from the iodine source to the iodine binding (capture) material. Increasing the flow rate or decreasing the amount of available iodine may reduce damage but also results in inadequate disinfecting.

The present inventor has realized an additional way to control the above-described process. Instead of providing successive columns of iodine source and iodine binding (capture) material there are profound advantages to using a mixed bed of both source and capture material. This may seem essentially counterintuitive because one might expect this mixed bed system to bypass the material to be disinfected with the iodine moving directly from the source to the capture material. However, when one realizes that the iodine is essentially insoluble in an aqueous medium without protein, it becomes apparent that iodine migration from source to capture material forms a circuit that must pass through the material to be disinfected. That is, the material to be disinfected picks up iodine at the source and almost instantly passes the iodine on to the capture material. However, in this "pass-through" process virus and other microbes are exposed to iodine and they may retain this iodine long enough and in sufficient quantity to effect complete disinfecting. Assuming that both the source and capture material have similar affinities for iodine, decreasing the ratio of source to capture material in a given mixture will have the effect of increasing the affinity of the source material for iodine. That is, from the perspective of the material to be disinfected less iodine will be available for binding much as if the affinity of the source had been increased. If necessary, a wider range of "affinities" can be made available by using different source and capture materials. A less obvious advantage of this approach is that it greatly increases the surface area on which iodine disinfecting can occur. This is because the added capture material quickly gains a surface iodine content. Because the affinity of the capture material is similar to the iodine source material in many cases, the capture material becomes capable of iodinating virus and other pathogens that come into physical contact with it. Thus, a relatively small amount of iodine can be spread over a large area and act as a "spider web" that targets passing pathogens.

Q-Sepharose has a relatively low affinity for iodine. This is beneficial if one wishes to release rapidly a relatively large quantity of iodine. Q-Sepharose can also function as a capture material to remove iodine but with a such relatively low affinity a comparatively large volume of Q Sepharose is needed to effectively capture iodine. When 45 ml of Q-Sepharose (30 ml Sepharose plus 15 ml water) was added to 250 ml of whole plasma and mixed thoroughly, it was found to provide protection against excess iodination. To the Sepharose-plasma mixture was added 40 ml of mixed iodinate/non-iodinated Sepharose (1 ml 10% iodine by weight Sepharose plus 4 ml of non-iodinated Sepharose plus 35 ml water) and mixed completely. Samples were removed at 15 min intervals and the Sepharose was then removed by filtration. The Sepharose filtered from the 15 min sample still showed brown iodine color. Tests indicated that the 15 min sample still showed significant activity of Factor VIII (an extremely iodine labile clotting factor). Later samples had lost virtually all their Factor VIII activity. This experiment indicated that a mixture of source and capture material was effective at modulating the over-iodination of clotting factors.

A similar approach was tried with virus-spiked plasma. Virus (either encephalo myocardiatis [EMC] or porcine parvo virus [PPV]) was added to 50 ml of human plasma. To each 50 ml aliquot 1.0 ml of iodinated Q-Sepharose (10% by weight iodine) plus 4.0 ml of non-iodinated Q-Sepharose were added and the samples were mixed for 60 min at room temperature. The Sepharose was then removed by filtration and serial dilutions of the treated samples were set up in a viral end point assay (VEPA). That is, the dilution was added to a nutrient plate containing a monolayer of test cells (vero, pk15 or bt, depending on the virus to be tested). After an appropriate incubation period (1–5 days) the plates were assayed for viral replication (formation of plaques). A score of 4 equals maximal plaque formation; a score of 1 shows slight plaque with a score of 0 indicating no signs of viral damage. In all cases there was no indication of cytotoxicity. This means there was essentially no free iodine in any of the samples. As is shown in the accompanying Table 2, the treatment resulted in essentially total kill of the virus.

TABLE 2

|  | 1 | 2 | 3 | 4 | 5 | 6 | 7 | 8 | 9 | 10 | 11 | 12 | Titer |
|---|---|---|---|---|---|---|---|---|---|---|---|---|---|
| EMC Control | 4 | 4 | 4 | 4 | 4 | 2 | 0 | 0 | 0 | 0 | 0 | 0 | 4.2 |
| EMC Test | 1 | 0 | 0 | 0 | 0 | 0 | 0 | 0 | 0 | 0 | 0 | 0 | 0 |
| PPV Control | 4 | 4 | 4 | 4 | 4 | 4 | 1 | 0 | 0 | 0 | 0 | 0 | 4.6 |
| PPV Test | 2 | 0 | 0 | 0 | 0 | 0 | 0 | 0 | 0 | 0 | 0 | 0 | 0.7 |

These results indicate that the mixture of iodinated and non-iodinated resin was able to effect excellent viral kill while leaving essentially no free iodine in the treated sample.

Table 3 shows a repeat of this experiment extended to include Bovine Diarrheal Virus (BVD). I this experiment the ratio of iodinated to non-iodinated resin was 1:3.

TABLE 3

|  | 1 | 2 | 3 | 4 | 5 | 6 | 7 | 8 | 9 | 10 | 11 | 12 | Titer |
|---|---|---|---|---|---|---|---|---|---|---|---|---|---|
| EMC Positive Control | 4 | 4 | 4 | 4 | 4 | 4 | 4 | 2 | 0 | 0 | 0 | 0 | 5.6 |
| EMC Negative Control | 0 | 0 | 0 | 0 | 0 | 0 | 0 | 0 | 0 | 0 | 0 | 0 | 0 |
| BMC Test | 0 | 0 | 0 | 0 | 0 | 0 | 0 | 0 | 0 | 0 | 0 | 0 | 0 |

TABLE 3-continued

|  | 1 | 2 | 3 | 4 | 5 | 6 | 7 | 8 | 9 | 10 | 11 | 12 | Titer |
|---|---|---|---|---|---|---|---|---|---|---|---|---|---|
| BVD Positive Control | 4 | 4 | 4 | 4 | 4 | 0 | 0 | 0 | 0 | 0 | 0 | 0 | 4.5 |
| BVD Negative Control | 0 | 0 | 0 | 0 | 0 | 0 | 0 | 0 | 0 | 0 | 0 | 0 | 0 |
| BVD Test | 4 | 4 | 4 | 1 | 0 | 0 | 0 | 0 | 0 | 0 | 0 | 0 | 2.6 |
| PPV Positive Control | 4 | 4 | 4 | 4 | 4 | 4 | 4 | 0 | 0 | 0 | 0 | 0 | 5.2 |
| BVD Negative Control | 0 | 0 | 0 | 0 | 0 | 0 | 0 | 0 | 0 | 0 | 0 | 0 | 0 |
| BVD Test | 4 | 4 | 4 | 4 | 4 | 3 | 0 | 0 | 0 | 0 | 0 | 0 | 4.4 |

These results show the differential sensitivities of various viruses. Presumably increasing the amount of iodinated resin or the incubation time would improve the kill of the more recalcitrant viruses.

A test was made of the effect of mixed iodinated and non-iodinated resin on whole blood. As explained above, the addition of significant amounts of iodine to whole blood results in gross hemolysis as the RBCs. Here iodinated (prepared by mixing 10 ml of resin in 40 ml of Lugol's solution (5% iodine-10% KI) for 24 hr) and non-iodinated Q-Sephrose "Big Bead" was employed. Forty milliliter aliquots of fresh whole blood were placed in 50 ml centrifuge tubes. To this was added either 1 ml iodinate Sepharose or a mixture of 1 ml iodinated Sepharose with 9 ml of non-iodinated Sepharose. The samples were incubated for 60 min, the Sepharose was removed by centrifugation, and the sample was observed for hemolysis. As expected, the sample with only iodinated Sepharose showed darkening of the RBCs and significant hemolysis. The control (no Sepharose) showed no hemolysis while the mixture of iodinated and non-iodinated Sepharose showed only slight hemolysis. This indicates that the mixed resin can offer significant protection to the RBCs. This is a worst case scenario because the incubation with the iodinated resin was for an extremely long time. In chromatographic processing (a preferred way of using the present invention) the contact time can be significantly more limited. Nevertheless, the mixed resin approach also shows considerable promise as a batch procedure albeit with incubation times of less than 60 min. These approaches offer a way to disinfect whole blood so that dangers of blood transfusion transmission of virus are eliminated. There have been some data that indicate that intracellular virus kill is possible. However, white blood cells remain a potential reservoir of virus. The present inventor contemplates removal of white blood cells from the disinfected whole blood, preferably before the iodine treatment. Many leukocyte filters are known in the art; the reader is referred to U.S. Pat. No. 5,639,376 and the references cited therein for details.

Because the present invention operates (in theory) partly by increasing the effective surface area of the iodine source, it has proven able to provide effective disinfecting at quite low iodine levels. A batch mode experiment was undertaken using iodinated DEAE Sephadex (anion exchange derivative of cross-linked dextran polymers made by Amersham-Pharmacia Biotech) and iodinated DEAE cellulose (the non-iodinated forms of each material served as a capture material. The anion exchange materials appear especially effective at iodine capture perhaps because they bind iodide ion which then renders elemental iodine more soluble and able to penetrate the resin. Quantities of iodinated and non-iodinated materials were weighed out into 50 ml sterile tubes as shown in Table 4.

TABLE 4

| | DEAE Sephadex | | DEAE Cellulose |
|---|---|---|---|
| | Non-iodinated | | Non-iodinated |
| a) | 1.0 g | a) | 1.0 g |
| b) | 0.5 g | b) | 0.5 g |
| c) | 0.25 g | c) | 0.25 g |
| d) | 0.1 g | d) | 0.1 g |
| | 50:50 1% iodinated/non-iodinated | | 50:50 1% iodinated/non-iodinated |
| e) | 2.0 g | e) | 2.0 g |
| f) | 1.0 g | f) | 1.0 g |
| g) | 0.5 g | g) | 0.5 g |
| h) | 0.25 g | h) | 0.25 g |
| i) | 0.1 g | i) | 0.1 g |
| | 50:50 0.5% iodinated/non-iodinated | | 50:50 0.5% iodinated/non-iodinated |
| j) | 2.0 g | j) | 2.0 g |
| k) | 1.0 g | k) | 1.0 g |
| l) | 0.5 g | l) | 0.5 g |
| m) | 0.25 g | m) | 0.25 g |
| n) | 0.1 g | n) | 0.1 g |

Twenty milliliters of a suspension of VSV (vesicular stomatitis virus) was dispensed into each tube and incubated with constant mixing at room temperature. After 30 min of settling, samples of each tube were set up in a VEPA assay as performed above. Results of the DEAE Sephadex experiment are given in Table 5 while the DEAE cellulose results are give in Table 6.

TABLE 5

DEAE Sephadex

| | 1 | 2 | 3 | 4 | 5 | 6 | 7 | 3 | 9 | 10 | 11 | 12 | 13 | 14 | 15 | Titer |
|---|---|---|---|---|---|---|---|---|---|---|---|---|---|---|---|---|
| a) | 4 | 4 | 4 | 4 | 4 | 4 | 4 | 4 | 1 | 0 | 0 | 0 | 0 | 0 | 0 | 6.0 |
| b) | 4 | 4 | 4 | 4 | 4 | 4 | 4 | 4 | 4 | 4 | 4 | 0 | 0 | 0 | 0 | 8.0 |
| c) | 4 | 4 | 4 | 4 | 4 | 4 | 4 | 4 | 4 | 4 | 4 | 4 | 2 | 0 | 0 | 9.1 |
| d) | 4 | 4 | 4 | 4 | 4 | 4 | 4 | 4 | 4 | 4 | 4 | 4 | 2 | 0 | 0 | 9.1 |
| e) | 0 | 0 | 0 | 0 | 0 | 0 | 0 | 0 | 0 | 0 | 0 | 0 | 0 | 0 | 0 | 0 |
| f) | 0 | 0 | 0 | 0 | 0 | 0 | 0 | 0 | 0 | 0 | 0 | 0 | 0 | 0 | 0 | 0 |
| g) | 4 | 0 | 0 | 0 | 0 | 0 | 0 | 0 | 0 | 0 | 0 | 0 | 0 | 0 | 0 | 1.0 |
| h) | 4 | 4 | 4 | 3 | 0 | 0 | 0 | 0 | 0 | 0 | 0 | 0 | 0 | 0 | 0 | 3.0 |
| i) | 4 | 4 | 4 | 4 | 4 | 4 | 4 | 0 | 0 | 0 | 0 | 0 | 0 | 0 | 0 | 5.2 |
| j) | 0 | 0 | 0 | 0 | 0 | 0 | 0 | 0 | 0 | 0 | 0 | 0 | 0 | 0 | 0 | 0 |
| k) | 4 | 4 | 2 | 0 | 0 | 0 | 0 | 0 | 0 | 0 | 0 | 0 | 0 | 0 | 0 | 2.1 |
| l) | 4 | 4 | 4 | 4 | 4 | 1 | 0 | 0 | 0 | 0 | 0 | 0 | 0 | 0 | 0 | 3.9 |
| m) | 4 | 4 | 4 | 4 | 4 | 4 | 4 | 0 | 0 | 0 | 0 | 0 | 0 | 0 | 0 | 5.2 |
| n) | 4 | 4 | 4 | 4 | 4 | 4 | 4 | 4 | 4 | 4 | 1 | 0 | 0 | 0 | 0 | 7.5 |
| C* | 4 | 4 | 4 | 4 | 4 | 4 | 4 | 4 | 4 | 4 | 4 | 4 | 2 | 0 | 0 | 9.1 |

*Control

TABLE 6

DEAE Cellulose

| | 1 | 2 | 3 | 4 | 5 | 6 | 7 | 3 | 9 | 10 | 11 | 12 | 13 | 14 | 15 | Titer |
|---|---|---|---|---|---|---|---|---|---|---|---|---|---|---|---|---|
| a) | 4 | 4 | 4 | 4 | 4 | 4 | 4 | 4 | 4 | 2 | 0 | 0 | 0 | 0 | 0 | 7.0 |
| b) | 4 | 4 | 4 | 4 | 4 | 4 | 4 | 4 | 4 | 4 | 4 | 4 | 2 | 0 | 0 | 9.1 |
| c) | 4 | 4 | 4 | 4 | 4 | 4 | 4 | 4 | 4 | 4 | 4 | 4 | 2 | 0 | 0 | 9.1 |
| d) | 4 | 4 | 4 | 4 | 4 | 4 | 4 | 4 | 4 | 4 | 4 | 4 | 2 | 0 | 0 | 9.1 |
| e) | 0 | 0 | 0 | 0 | 0 | 0 | 0 | 0 | 0 | 0 | 0 | 0 | 0 | 0 | 0 | 0 |
| f) | 0 | 0 | 0 | 0 | 0 | 0 | 0 | 0 | 0 | 0 | 0 | 0 | 0 | 0 | 0 | 0 |
| g) | 4 | 4 | 2 | 0 | 0 | 0 | 0 | 0 | 0 | 0 | 0 | 0 | 0 | 0 | 0 | 2.1 |
| h) | 4 | 4 | 4 | 4 | 4 | 4 | 4 | 0 | 0 | 0 | 0 | 0 | 0 | 0 | 0 | 5.2 |
| i) | 4 | 4 | 4 | 4 | 4 | 4 | 4 | 4 | 1 | 0 | 0 | 0 | 0 | 0 | 0 | 6.0 |
| j) | 0 | 0 | 0 | 0 | 0 | 0 | 0 | 0 | 0 | 0 | 0 | 0 | 0 | 0 | 0 | 0 |
| k) | 4 | 4 | 2 | 0 | 0 | 0 | 0 | 0 | 0 | 0 | 0 | 0 | 0 | 0 | 0 | 2.1 |
| l) | 4 | 4 | 4 | 3 | 0 | i | 0 | 0 | 0 | 0 | 0 | 0 | 0 | 0 | 0 | 3.0 |
| m) | 4 | 4 | 4 | 4 | 4 | 4 | 4 | 0 | 0 | 0 | 0 | 0 | 0 | 0 | 0 | 5.2 |
| n) | 4 | 4 | 4 | 4 | 4 | 4 | 4 | 4 | 4 | 4 | 1 | 0 | 0 | 0 | 0 | 7.5 |
| C* | 4 | 4 | 4 | 4 | 4 | 4 | 4 | 4 | 4 | 4 | 4 | 4 | 2 | 0 | 0 | 9.1 |

*Control

These results show that even low levels of iodine (0.5%) can effectively disinfect solution when combined with a capture agent to increase the iodine surface area. As has been reported in the prior art, virus particle appear to bind to plain DEAE resins resulting in up to a 3 log decrease in virus count.

A similar experiment was then performed using also low affinity resins such as the anion exchange resins (Purolite) shown above. For this experiment the following materials were weighed into 50 ml tubes:

a) 4.0 g DEAE Sephadex
b) 4.0 g of 50:50 5% iodine DEAE Sephadex/plain DEAE Sephadex
c) 4.0 g DEAE Cellulose
d) 4.0 g of 50:50 5% iodine DEAE Cellulose/plain DEAE Cellulose
e) 4.0 g anion exchange resin (Purolite A606)
f) 4.0 g 50:50 mixture 5% iodine anion exchange (Purolite A605)/plain anion exchange resin (Purolite "Purodine" A605)

Each aliquot of resin was mixed with 25 ml of VSV virus in tissue culture medium. As before the tubes were mixed for 60 min at room temperature and then allowed to settle for 30 min prior to samples being set up in a VEPA. The results are shown in Table 7.

TABLE 7

| | 1 | 2 | 3 | 4 | 5 | 6 | 7 | 3 | 9 | 10 | 11 | 12 | 13 | 14 | 15 | Titer |
|---|---|---|---|---|---|---|---|---|---|---|---|---|---|---|---|---|
| a) | 4 | 4 | 4 | 4 | 4 | 4 | 3 | 0 | 0 | 0 | 0 | 0 | 0 | 0 | 0 | 5.1 |
| b) | 0 | 0 | 0 | 0 | 0 | 0 | 0 | 0 | 0 | 0 | 0 | 0 | 0 | 0 | 0 | 0 |
| c) | 4 | 4 | 4 | 4 | 4 | 4 | 4 | 0 | 0 | 0 | 0 | 0 | 0 | 0 | 0 | 5.2 |

TABLE 7-continued

|   | 1 | 2 | 3 | 4 | 5 | 6 | 7 | 8 | 9 | 10 | 11 | 12 | 13 | 14 | 15 | Titer |
|---|---|---|---|---|---|---|---|---|---|----|----|----|----|----|----|-------|
| d) | 0 | 0 | 0 | 0 | 0 | 0 | 0 | 0 | 0 | 0 | 0 | 0 | 0 | 0 | 0 | 0 |
| e) | 4 | 4 | 4 | 4 | 4 | 4 | 4 | 4 | 1 | 0 | 0 | 0 | 0 | 0 | 0 | 6.0 |
| f) | 4 | 4 | 3 | 0 | 0 | 0 | 0 | 0 | 0 | 0 | 0 | 0 | 0 | 0 | 0 | 2.3 |
| C* | 4 | 4 | 4 | 4 | 4 | 4 | 4 | 4 | 4 | 4 | 4 | 4 | 4 | 1 | 0 | 9.5 |

*Control

These results show that the "spider web" approach is quite effective. Most interesting is the results with using a high affinity resin all by itself (e) as opposed to using half the amount of iodine source resin with an equal weight of iodine capture resin. Because of the weight of iodine, the volume of the capture resin considerably exceeded that of the iodine source resin. This illustrates the importance of having adequate surface area to effect pathogen kill.

The very low iodine "spider web" approach is also effective in chromatographic approaches to iodine disinfecting. In this experiment the following columns were prepared in duplicate: a) 50:50 mix of 5% iodine (by weight) DEAE Sephadex (2.0 g) and non-iodinated DEAE Sephadex (2.0 g); b) 50:50 mix 2.5% iodine (by weight) DEAE Sephadex (2.0 g) and non-iodinated DEAE Sephadex (2.0 g); and c) 4.0 g of non-iodinated DEAE Sephadex. Aliquots of human plasma (50 ml each) were spiked with either BVD virus or PPV virus. The samples were allowed to filter through the columns by gravity flow (approximate flow rate 5 ml/min). The samples were immediately placed on VEPA performed as above. The results are shown below in Table 8.

TABLE 8

|   | 1 | 2 | 3 | 4 | 5 | 6 | 7 | 8 | 9 | 10 | 11 | 12 | Titer |
|---|---|---|---|---|---|---|---|---|---|----|----|----|-------|
| BVD |   |   |   |   |   |   |   |   |   |   |   |   |   |
| a) | 0 | 0 | 0 | 0 | 0 | 0 | 0 | 0 | 0 | 0 | 0 | 0 | 0 |
| b) | 4 | 4 | 2 | 0 | 0 | 0 | 0 | 0 | 0 | 0 | 0 | 0 | 2.1 |
| c) | 4 | 4 | 4 | 4 | 4 | 0 | 0 | 0 | 0 | 0 | 0 | 0 | 3.8 |
| C* | 4 | 4 | 4 | 4 | 4 | 4 | 2 | 0 | 0 | 0 | 0 | 0 | 4.9 |
| PPV |   |   |   |   |   |   |   |   |   |   |   |   |   |
| a) | 0 | 0 | 0 | 0 | 0 | 0 | 0 | 0 | 0 | 0 | 0 | 0 | 0 |
| b) | 4 | 4 | 4 | 4 | 1 | 0 | 0 | 0 | 0 | 0 | 0 | 0 | 3.3 |
| c) | 4 | 4 | 4 | 4 | 2 | 0 | 0 | 0 | 0 | 0 | 0 | 0 | 3.5 |
| C* | 4 | 4 | 4 | 4 | 4 | 4 | 4 | 2 | 0 | 0 | 0 | 0 | 5.6 |

*Control

These data show that while the resin itself does bind a certain amount of virus, the addition of iodine can cause complete inactivation if sufficient surface area is provided.

The foregoing experiments demonstrate the efficacy of using mixed iodinated and non-iodinated resins to protect labile cells or proteins while simultaneously killing pathogens. These experiments also demonstrate the problem with using high affinity resins (e.g. Purolite) or resins with insufficient affinity (e.g. Sepharose). While the low affinity resin may be a good iodine source, it is generally a fairly poor capture agent. What is needed is an extremely rapid/high affinity capture agent combined with a good iodine (i.e., not too high affinity) iodine source. In terms of capture ability affinity does not necessarily predict rapidity of capture. The Purolite anion exchange resins bind iodine with high affinity and release it only slowly. However, these same materials take up iodine only slowly so that they do not act as ideal capture materials. The present inventor has found that a series of iodinated and capture resins produced by Umpqua Research (Myrtle Creek, Oreg.) can be especially effective in the present invention. The Umpqua resins were designed for use in water purification. The iodinated resin (MCV) appears to be somewhat less avid than Purolite as judged by hemolysis and effects on labile proteins (below). The capture resin "Iodosorb" is an extremely rapid absorber of both iodine (elemental iodine) and iodide so that both the added iodine and its reaction product are removed. At the current time these appear to be the most ideal resins available in that the Iodosorb removes iodine and iodide more rapidly than any other known capture agent. This should lead to the least possible amount of over-iodination damage.

For initial experiments individual columns for iodine (MCV) and for capture (Iodosorb) columns were set up in series so that liquid to be treated could be rapidly pumped through the Iodine source column and then through the Capture column to rapidly remove any elemental iodine and free iodide ion. It was hoped that by using a fast flow rate the amount of excess iodination damage would be limited because the iodine would be very rapidly removed by the Capture column. The treatment columns used were 750 ml each and the experiment was adjusted so that the sample flow rate was 100 ml per minute. For the initial experiment frozen human plasma (500 ml samples) was defrosted and either run as is or after addition of PPV as a test of the disinfecting ability of the system. VEPA demonstrated an essentially complete viral kill. However, blood chemistry analysis indicated a significant loss of activity in key blood enzymes and an extreme increase in clotting time (PT and aPTT). This indicates that in spite of the rapid and effective capture of iodine considerable iodine-induced damage to the vital proteins was still occurring. Table 9 shows the results of this experiment

TABLE 9

| Test | Pre-run | Iodine Treated |
|------|---------|----------------|
| Total Protein (g/dl) | 7.5 | 7.5 |
| Albumin (g/dl) | 4.8 | 4.6 |
| Alkaline Phosphatase (u/L) | 45 | 43 |
| LDH (IU/L) | 117 | 10 |
| CPK (IU/L) | 102 | 3 |
| SGOT (u/L) | 41 | 19 |
| SGPT (u/L) | 17 | 10 |
| GGT (u/dl) | 32 | 22 |
| Lipase (u/L) | 12 | 10 |
| Uric Acid (mg/dl) | 7.5 | 2.0 |

TABLE 9-continued

| Test | Pre-run | Iodine Treated |
|---|---|---|
| Chloride (mEq/L) | 108 | 90 |
| PT | 10 sec | >45 sec* |
| aPTT | 12 sec | >45 sec** |

*normal range = 10–20 sec.
**normal range 10–15 sec.

There was no detectable free (elemental) iodine or iodide in the treated samples. Notice that many of the blood enzyme values are strongly decreased by the iodine treatment. Some part of the decrease might be due to selective binding of the enzyme to the Iodosorb capture material because this material is a strong anion exchanger. However, total protein is unchanged by the treatment suggesting that most of the enzyme decrease is due to iodine damage to the enzyme. Changes in uric acid are probably due to oxidation by iodine Changes in chloride may be due to binding to the Iodosorb. This is somewhat discouraging because this of the seemingly perfect properties of the iodination and capture material. One way of decreasing iodine damage might be to increase the flow rate so that iodine contact time would be further decreased. The drawback is the difficulty in ensuring sufficiently high flow rates. Similarly, reducing the volume of the iodination resin can also reduce the iodine effect. However, these changes also introduce the risk of inadequate disinfection (i.e., insufficient iodine to kill or inactivate all microbes).

Some of these options were explored in a second experiment shown in Table 10. Here 500 ml aliquots of thawed human plasma were again treated with 750 ml iodination columns (equivalent samples with and without PPV were run). This time, however, the column was run at either 50, 100 or 200 ml/min and the effluent was deposited in a solution of 10 mg/ml sodium ascorbate to ensure rapid neutralization of the iodine. All iodine color disappeared immediately upon contact with the ascorbate solution. Following neutralization the solutions were run through the capture column to remove iodide. Significantly, the blood chemistry was checked after neutralization and after capture.

TABLE 10

| Test | Pre-run | After Ascorbate (50/100/200) | | | After Capture (50/100/200) | | |
|---|---|---|---|---|---|---|---|
| Total Protein (g/dl) | 7.5 | 7.5 | 7.5 | 7.5 | 7.4 | 7.5 | 7.5 |
| Albumin (g/dl) | 4.7 | 4.8 | 4.7 | 4.8 | 4.7 | 4.8 | 4.8 |
| Akaline Phosphatase (u/L) | 45 | 42 | 43 | 43 | 42 | 42 | 43 |
| LDH (IU/L) | 117 | 51 | 68 | 82 | 50 | 70 | 81 |
| CPK (IU/L) | 98 | 5 | 28 | 51 | 6 | 28 | 51 |
| SGOT (u/L) | 42 | 10 | 23 | 36 | 10 | 24 | 36 |
| SGPT (u/L) | 12 | 4 | 8 | 12 | 3 | 8 | 11 |
| GGT (u/dl) | 20 | 21 | 20 | 20 | 20 | 19 | 20 |
| Lipase (u/L) | 7 | 7 | 6 | 7 | 7 | 7 | 7 |
| Uric Acid (mg/dl) | 7.1 | 1.8 | 2.5 | 3.6 | 1.9 | 2.5 | 3.7 |
| Chloride (mEq/L) | 98 | 190 | 191 | 184 | 72 | 81 | 75 |
| PT | 12 sec | >45 sec* (all flow rates) | | | >45 sec* (all flow rates) | | |
| aPTT | 10 sec | >45 sec** (all flow rates) | | | >45 sec** (all flow rates) | | |

*normal range = 10–20 sec.
**normal range = 10–15 sec.

These results indicate most of the changes in blood chemistry are due to iodine reaction and not to some effect of the capture material. In all cases there was neither detectable free iodine nor iodide in the treated blood. The labile enzymes are somewhat spared by faster flow rate (less iodine contact time). Even the change in apparent uric acid content appears to be due to iodine reaction. The chloride loss is probably due to the capture column. The anomalous high readings following ascorbate neutralization appear to be from ascorbate interference. The clotting times (PT and aPTT) were maximally effected by any iodine contact. In all of the iodine treatments, regardless of flow rate, there was complete kill of the added PPV.

Experiments were then undertaken to explore the effect of lowering iodine availability by mixing the iodine source and capture materials. The experiment of Table 4 was repeated except that each of the 750 ml column contained a 50:50 mixture of the iodine source and iodine capture resins. Again 500-ml aliquots of thawed frozen human plasma were run (with or without PPV addition). It will be appreciated that a 50:50 mixture might not be adequate. If needed more iodine, can be provided by increasing the proportion of iodine source resin. If over-iodination is apparent, a larger proportion of the iodine capture resin can be used. Although one might expect that mixing the two resins would result in less effective disinfecting, the results showed that the mixed resin system was as effective, or even more effective, than non-mixed resin. Here the total amount of iodine-donating resin was the same as in earlier experiments. However, mixed resin also showed excellent disinfecting using volumes of iodine-donating resin that was inadequate when used by itself. A likely explanation is that effective iodine disinfecting is related to the available surface area on which iodine is present. As protein solutions flow through a mixed-resin system, iodine is rapidly carried to the capture surface, which then becomes an effective disinfecting agent. The mixed-resin results are shown in Table 11.

TABLE 11

| Test | Pre-run | Iodine Treated |
|---|---|---|
| Total Protein (g/dl) | 7.6 | 7.6 |
| Albumin (g/dl) | 4.8 | 4.7 |
| Alkaline Phosphatase (u/L) | 47 | 46 |
| LDH (IU/L) | 120 | 100 |
| CPK (IU/L) | 99 | 90 |
| SGOT (u/L) | 45 | 43 |
| SGPT (u/L) | 19 | 18 |
| GGT (u/dl) | 25 | 25 |
| Lipase (u/L) | 9 | 8 |
| Uric Acid (mg/dl) | 6.5 | 4.0 |
| Chloride (mEq/L) | 109 | 90 |
| PT | 10 sec | 20 sec* |
| aPTT | 12 sec | 15 sec** |

*normal range = 10–20 sec.
**normal range = 10–15 sec.

Again neither free iodine nor iodide were detectable in the treated samples. As compared to the non-mixed resin, the sparing of the blood enzymes is quite striking. Even the extremely sensitive clotting times fell barely within the normal ranges. There is every reason to expect these results to be improved by "fine tuning" the ratio of iodine-donating to iodine-capturing resin. Further, it was discovered that the mixed resin columns are quite stable when stored in water; probably because the solubility of iodine within water is quite low.

This same experiment was repeated using fresh (as opposed to thawed frozen) human plasma. It is known that freeze-thawing partially damages many enzymes. It was though that native enzymes might better withstand the assault of iodine. These results are shown below in Table 12. Again, the experiment resulted in complete destruction of added PPV.

TABLE 12

| Test | Pre-run | Iodine Treated |
| --- | --- | --- |
| Total Protein (g/dl) | 7.5 | 7.5 |
| Albumin (g/dl) | 4.8 | 4.6 |
| Alkaline Phosphatase (u/L) | 50 | 49 |
| LDH (IU/L) | 101 | 99 |
| CPK (IU/L) | 98 | 98 |
| SGOT (u/L) | 41 | 40 |
| SGPT (u/L) | 15 | 15 |
| GGT (u/dl) | 23 | 24 |
| Lipase (u/L) | 5 | 5 |
| Uric Acid (mg/dl) | 6.5 | 5.9 |
| Chloride (mEq/L) | 106 | 92 |
| PT | 10 sec | 11 sec* |
| aPTT | 11 sec | 11 sec** |

*normal range = 10–20 sec.
**normal range = 10–15 sec.

All detectable iodine and iodide were removed from the samples by the treatment. Here the mixed-resin system caused even less loss of enzyme function than with thawed frozen plasma. This indicates the tremendous utility of using mixed-resin (iodine source:iodine capture) for disinfecting plasma and other protein solutions while causing a minimum of iodine-induced damage.

While these experiments have demonstrated a 50:50 (source:capture) mixture, it is obvious that a wide range of mixtures can be useful. If the 50:50 mixture shows unacceptable protein damage at a given flow rate, the proportion of capture should be increased. Preliminary experiments have shown useful results with ratios as low as 1:99. The major problem with such low ratios is that the iodine source is very quickly exhausted. This can be partially remedied by increasing the total size of the column used as compared to the size of the sample. However, this leads to excess loss of sample on the column. A better solution is to increase the flow rate to lower protein damage before lowering the ratio below 10:90. Similarly, if VEPA teats show that the 50:50 mixture results in insufficient disinfecting, the flow rate should be lowered and/or the ratio increased. Preliminary experiments show that ratios above 75:25 tend to behave more like pure iodine source in terms of protein damage. However, this can be readily explored on a case by case basis.

These experiments have mostly been performed using mixtures in which the iodine source and the iodine capture resin are fairly similar chemically (e.g. Umpqua resins). However, there is no reason that the effective range of the ratios cannot be extended by using mixtures of disparate materials. It is believed that the best results will occur with capture resins showing a very rapid binding of iodine. However, there may be distinct advantages in using an iodine source that has relatively low iodine affinity. This will allow low ratio (e.g., 10:90 or lower) mixtures to effectively disinfect. This may be useful for extremely labile proteins. Materials such as agarose or dextran polymers (Sepharose and Sephadex, products of Amersham-Pharmacia-Biotech) appear to be ideal low affinity iodine sources. While blood-based liquids are illustrated herein, experiments have shown that the method disinfects virtually any protein-containing solution. Also, the mixed-resin spider web approach allows ready treatment of fruit juice, milk and other liquid foods while minimizing damage to delicate flavors, etc.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

What is claimed is:

1. A method for killing or inactivating microbes in a liquid without inactivating proteins and other labile constituents in the liquid comprising the steps of:

contacting the liquid with a mixture of insoluble particles of an elemental iodine-containing material, which material acts as a source for elemental iodine, and of insoluble particles of an insoluble iodine-binding material, which material acts as a sink for elemental iodine; and removing the mixture of particles from the liquid.

2. The method of claim 1, wherein the elemental iodine-containing material is selected from the group consisting of iodinated agarose, iodinated crosslinked dextrans, iodinated DEAE cellulose, iodinated polyvinyl acetal, iodinated polyvinyl pyrollidone and iodinated styrene-divinyl benzene anion exchange resin.

3. The method of claim 1, wherein the iodine-binding material is selected from the group consisting of agarose, crosslinked dextrans, DEAE cellulose, polyvinyl acetal, cross-linked polyvinyl pyrollidone and iodinated styrene-divinyl benzene anion exchange resin.

4. The method of claim 1, wherein a proportion of the elemental iodine-containing material to the iodine-binding material is between 1:99 and 90:10 by weight.

5. The method of claim 1, wherein a proportion of the elemental iodine-containing material to the iodine-binding material is between 1:99 and 90:10 by weight.

6. A method for killing or inactivating microbes in a liquid without inactivating proteins and other labile constituents in the liquid comprising flowing the liquid through a mixture of insoluble particles of an elemental iodine-containing material, which material acts as a source for elemental iodine, and of insoluble particles of an insoluble iodine-binding material, which material acts as a sink for elemental iodine.

7. The method of claim 6, wherein the elemental iodine-containing material is selected from the group consisting of iodinated agarose, iodinated crosslinked dextrans, iodinated DEAE cellulose, iodinated polyviny acetal, iodinated cross-linked polyvinyl pyrollidone and iodinated styrene-divinyl benzene anion exchange resin.

8. The method of claim 6, wherein the iodine-binding material is selected from the group consisting of agarose, crosslinked dextrans, DEAE cellulose, polyvinyl acetal, cross-linked polyvinyl pyrollidone and styrene-divinyl benzene anion exchange resin.

9. The method of claim 6, wherein a proportion of the elemental iodine-containing material to the iodine-binding material is between 1:99 and 90:10 by weight.

10. The method of claim 9, wherein a proportion of the elemental iodine-containing material to the iodine-binding material is between 1:99 and 90:10 by weight.

* * * * *